United States Patent [19]

Finkelstein et al.

[11] Patent Number: 5,241,966
[45] Date of Patent: Sep. 7, 1993

[54] METHOD AND APPARATUS FOR MEASURING CARDIAC OUTPUT

[75] Inventors: Stanley M. Finkelstein, St. Louis Park; Jay N. Cohn, Minneapolis, both of Minn.

[73] Assignee: Hypertension Diagnostics, Inc., South St. Paul, Minn.

[21] Appl. No.: 978,179

[22] Filed: Nov. 17, 1992

Related U.S. Application Data

[63] Continuation of Ser. No. 601,460, Oct. 23, 1990, abandoned.

[51] Int. Cl.$^5$ .............................................. A61B 5/029
[52] U.S. Cl. .................................... 128/713; 128/687; 128/672
[58] Field of Search ................ 128/672, 673, 687–689, 128/713

[56] References Cited

U.S. PATENT DOCUMENTS

| | | | |
|---|---|---|---|
| 4,137,910 | 2/1979 | Murphy | 128/713 X |
| 4,562,843 | 1/1986 | Djordjevich et al. | 128/672 |
| 4,807,638 | 2/1989 | Sramek | 128/672 |

OTHER PUBLICATIONS

Study, "Trending Cardiac Output in Surgical ICU Patients Using the Pulse Contour Method," G. A. Tannenbaum et al., Columbia University, Mar. 5, 1992.
R. M. Cundick, Jr. et al., "Clinical Comparison of Pressure-Pulse and Indicator-Dilution Cardiac Output Determination", *Circulation* 62, pp. 371–376 (1980).
H. R. Warner et al., "Computer-Based Monitoring of Cardiovascular Functions in Postoperative Patients", *Circulation* 37 (Suppl. II), pp. II-68–II-74 (1968).
N. T. Kouchoukos et al., "Estimation of Stroke Volume in the Dog by a Pulse Contour Method", *Circulation Research* 26, pp. 611–623 (1970).
T. Tajimi et al., "Evaluation of Pulse Contour Methods in Calculating Stroke Volume from Pulmonary Artery Pressure Curve (Comparison with Aortic Pressure Curve)", *European Heart Journal* 4, pp. 502–511 (1983).
D. F. Opdyke, "Genesis of the Pressure Pulse Contour Method for Calculating Cardiac Stroke Index", *Federation Proceedings* 11, pp. 733–737 (1952).
H. R. Warner et al., "Quantitation of Beat-to-Beat Changes in Stroke Volume From the Aortic Pulse Contour in Man", *J. Appl. Physiol.* 5, pp. 495–507 (1953).
C. F. Starmer et al., "Evaluation of Several Methods for Computing Stroke Volume from Central Aortic Pressure", *Circulation Research* 33, pp. 139–148 (1973).
M. J. Bourgeois et al., "Continuous Determination of Beat-to-Beat Stroke Volume from Aortic Pressure Pulses in the Dog", *Circulation Research* 39, pp. 15–24 (1976).
E. L. Alderman et al., "Evaluation of the Pulse-Contour Method of Determining Stroke Volume in Man", *Circulation* 46, pp. 546–558 (1972).
J. B. English et al., "Comparison of Aortic Pulse-wave Contour Analysis and Thermodilution Methods of Measuring Cardiac Output During Anesthesia in the Dog", *Anesthesiology* 52, pp. 56–61 (1980).
H. Smulyan et al., "An Evaluation of the Cardiac Index", *American Heart Journal* 72(S), pp. 621–631 (1966).
L. J. Krovetz, "Normal Standards for Cardiovascular Data I. Examination of the Validity of Cardiac Index", *Johns Hopkins Medical Journal* 130(3), pp. 174–186, (1972).

(List continued on next page.)

Primary Examiner—Lee S. Cohen
Assistant Examiner—Kevin Pontius
Attorney, Agent, or Firm—Merchant, Gould, Smith, Edell, Welter & Schmidt

[57] ABSTRACT

Apparatus for Measuring Stroke Volume/Cardiac Output includes a transducer for measuring arterial blood pressure waveform, a digitizer for digitizing the analog signal generated by the transducer and a digital signal processor for determining ejection time and heart rate. Processor circuitry determines cardiac output using the ejection time, heart rate, the body surface area and age of the patient, with the cardiac output measure being displayed by the meter.

15 Claims, 5 Drawing Sheets

OTHER PUBLICATIONS

A. M. Weissler et al., "Relationships Between Left Ventricular Ejection Time, Stroke Volume, and Heart Rate in Normal Individuals and Patients with Cardiovascular Disease", *Am. Heart J.* 62, p. 367-378 (1961).

J. W. Remington, "Volume Quantitation of the Aortic Pressure Pulse", *Federation Proceedings* 11, pp. 750-761 (1952).

R. S. Alexander, "Factors Determining the Contour of Pressure Pulses Recorded From the Aorta", *Federation Proceedings* 11, pp. 738-749 (1952).

P. Lompard et al., "Effect of Posture on the Length of the Systole of the Human Heart", *Am. J. Physiol.* 40, pp. 140-141 (1919).

M. J. Bourgeois et al., "Characteristics of Aortic Diastolic Pressure Decay with Application to the Continuous Monitoring of Changes in Peripheral Vascular Resistance", *Circulation Research* 35, pp. 56-66 (1974).

A. M. Weissler et al., "Systolic Time Intervals in Heart Failure in Man", *Circulation* 37, pp. 149-159 (1968).

M. A. Stefadouros et al., "The Efect of Isometric Exercise on the Left Ventricular Volume in Normal Man", *Circulation* 49, pp. 1185-1189 (1974).

E. Braunwald et al., "Determinants of Duration and Mean Rate of Ventricular Ejection", *Circulation Research* 6, pp. 319-325 (1958).

A. G. Wallace et al., "Duration of the Phases of Left Ventricular Systole", *Circulation Research* 12, pp. 611-619 (1963).

Stanley M. Finkelstein et al., "Arterial Vascular Compliance Responses to Vasodilators by Fourier and Pulse Contour Analysis", *Hypertension* 12, pp. 380-387 (1988).

Homer R. Warner, "The Role of Computers in Medical Research", *JAMA* 196 (11), pp. 944-949 (1966).

A. Harley et al, "Pressure-Flow Studies in Man. An Evaluation of the Duration of the Phases of Systole", *The Journal of Clinical Investigation* 48, pp. 895-905 (1969).

J. W. Remington et al., "Formation of Peripheral Pulse Contour in Man", *J. Appl. Physiol.* 9, pp. 433-442 (1952).

J. Alan Herd et al., "Arterial Pressure Pulse Contours During Hemorrhage in Anesthetized Dogs", *J. Appl. Physiol.* 21 (6), pp. 1864-1868 (1966).

P. Cinnelli et al., "Systolic Time Intervals During Isometric Exercise in Supine Position Should be Corrected Also for Arterial Pressure", *Acta Cardiologica* 37 (2), pp. 93-103.

J. Willems, et al., "The Left Ventricular Ejection Time. Its Relation to Heart Rate, Mechanical Systole and Some Anthropometric Data", *Acta Cardiologica* 22, pp. 401-425 (1967).

D. A. McDonald, *Blood Flow in Arteries*, Williams & Wilkins Co., Baltimore, pp. 258-281 (1960).

A. Holmgren et al., "Circulatory Data in Normal Subjects at Rest and During Exercise in Recumbent Position, with Special Reference to the Stroke Volume at Different Work Intensities", *Acta Physiol. Scand.* 49, pp. 343-363 (1960).

"Systolic Time Intervals Reconsidered, Reevaluation of the Preejection Period: Absence of Relation to Heart Rate," by D. H. Spodick et al., *The American Journal of Cardiology*, vol. 53, pp. 1667-1670 (Jun. 1, 1984).

"Systolic Time Intervals at Rest and During Exercise," by D. Cardus and L. Vera, *Cardiology*, vol. 59, pp. 133-153 (1974).

"The Mechanics of the Circulation," by C. G. Caro et al., *Oxford Medical Publications*, pp. 268-278 (1978).

Article, L.-G. Ekman et al., "Clinical Evaluation of an Ensemble-Averaging Impedance Cardiograph for Monitoring Stroke Volume During Spontaneous Breathing", *Acta Anaesthesiol Scand*, 34: 190-196 (1990).

METHOD AND APPARATUS FOR MEASURING CARDIAC OUTPUT

This is a continuation of application Ser. No. 601,460, filed Oct. 23, 1990, now abandoned.

TECHNICAL FIELD OF THE INVENTION

The present invention pertains generally to the field of medicine, and more particularly to cardiology and biomedical engineering.

BACKGROUND OF THE INVENTION

Cardiac output is an important hemodynamic variable widely used in the field of cardiology for diagnosis and other characterizations of the cardiovascular system. It is routinely used as a diagnostic measure of cardiac function, particularly in the diagnosis of congestive heart failure and related cardiac disease. Characterizations of the cardiovasculature using the Windkessel model, employed to obtain measures of vascular compliance, also require a measure of cardiac output.

Thermodilution and dye dilution procedures are considered two of the most accurate measures of cardiac output. They are, however, surgically invasive procedures which require catheterization of the subject. As such, these procedures are inconvenient, time consuming and expensive, as well as undesirable from the patient's perspective. Moreover, notwithstanding the fact that they are considered the most accurate measures of cardiac output, they have a reproducibility of only between ten to twenty percent. Other measures of cardiac output include: "eyeball" estimates, made on the basis of the patients size and subject to considerable error; Doppler measurement techniques which measure blood velocity and calculate output based on a further measure of aorta cross section, and which are time consuming and subject to errors in aorta cross section measurement; and rebreathing techniques, which are considered difficult to implement, and subject to considerable error if not executed with great care. The Minnesota Thoracic Impedance method, a non-invasive measure of cardiac output, is another alternative measure. While this method may be adequate for detecting changes in cardiac output, it is poor at measuring the absolute value of cardiac output.

Others have devised procedures for measuring cardiac output based on measurements of body surface area, age, heart rate, weight, height and ejection time, whereby a quick, non-invasive measure of cardiac output can be obtained. For example, Smulyan et al., in "An Evaluation of the Cardiac Index," disclose a method for measuring cardiac output using a subject's height and weight (factors closely related to body surface area); Krovetz and Goldbloom, in "Normal Standards for Cardiovascular Data—I. Examination of the Validity of Cardiac Index," disclose a method using age, height, weight and heart rate; and Weissler et al., in "Relationships Between Left Ventricular Ejection Time, Stroke Volume, and Heart Rate in Normal Individuals and Patients with Cardiovascular Disease," establish some correlation between ejection time and cardiac output. While these procedures are relatively fast and easy compared to others, and thus are indicated over the slower, more cumbersome and invasive procedures, they are generally less accurate measures of cardiac output. The present invention provides a measure of cardiac output, in the genre of these procedures, with acceptable accuracy for many applications.

SUMMARY OF THE INVENTION

According to the apparatus of the invention, there is provided a cardiac output meter having transducer means for measuring the blood pressure waveform of the patient and generating a corresponding analog signal, means for digitizing the analog signal generated by the transducer means, means for determining, by digital signal processing of the digitized blood pressure waveform, the ejection time and heart rate, and means for calculating and displaying a measure of cardiac output based on the heart rate, ejection time, and the patient's body surface area and age.

According to another aspect of the meter, there is included means for automatically determining the body surface area by standard formula or nomogram, based on input variables including the subject's height and weight.

According to the method of the present invention, there is measured, either noninvasively or invasively, an arterial blood pressure waveform. The waveform data are processed to determine the ejection time of the heart. The heart rate is measured, and body surface area is determined by standard formula or by nomogram, using the subject's height and weight. Stroke volume is then determined in accordance with the following formula:

$$SVA = -6.6 + 0.25 \times ET + 40.4 \times BSA - 0.5 - 1 \times Age - 0.62 \times HR,$$

where SVA equals stroke volume in ml/beat, ET is ejection time in msec, BSA is body surface area in square meters, Age is the age of the subject, and HR is heart rate (beats per minute). Cardiac output is determined by multiplying SVA times the heart rate HR.

The present invention thus provides method and apparatus for determining cardiac output without special instrumentation beyond that normally required for hemodynamic monitoring or vascular compliance determination. The invention requires no calibration, is easily applied, can be done noninvasively, and, even if done invasively, is much simpler than the standard dilution technique. The invention thus has considerable potential for use in screening subjects based on stroke volume/cardiac output determinations.

DETAILED DESCRIPTION OF THE INVENTION

Figure 1:
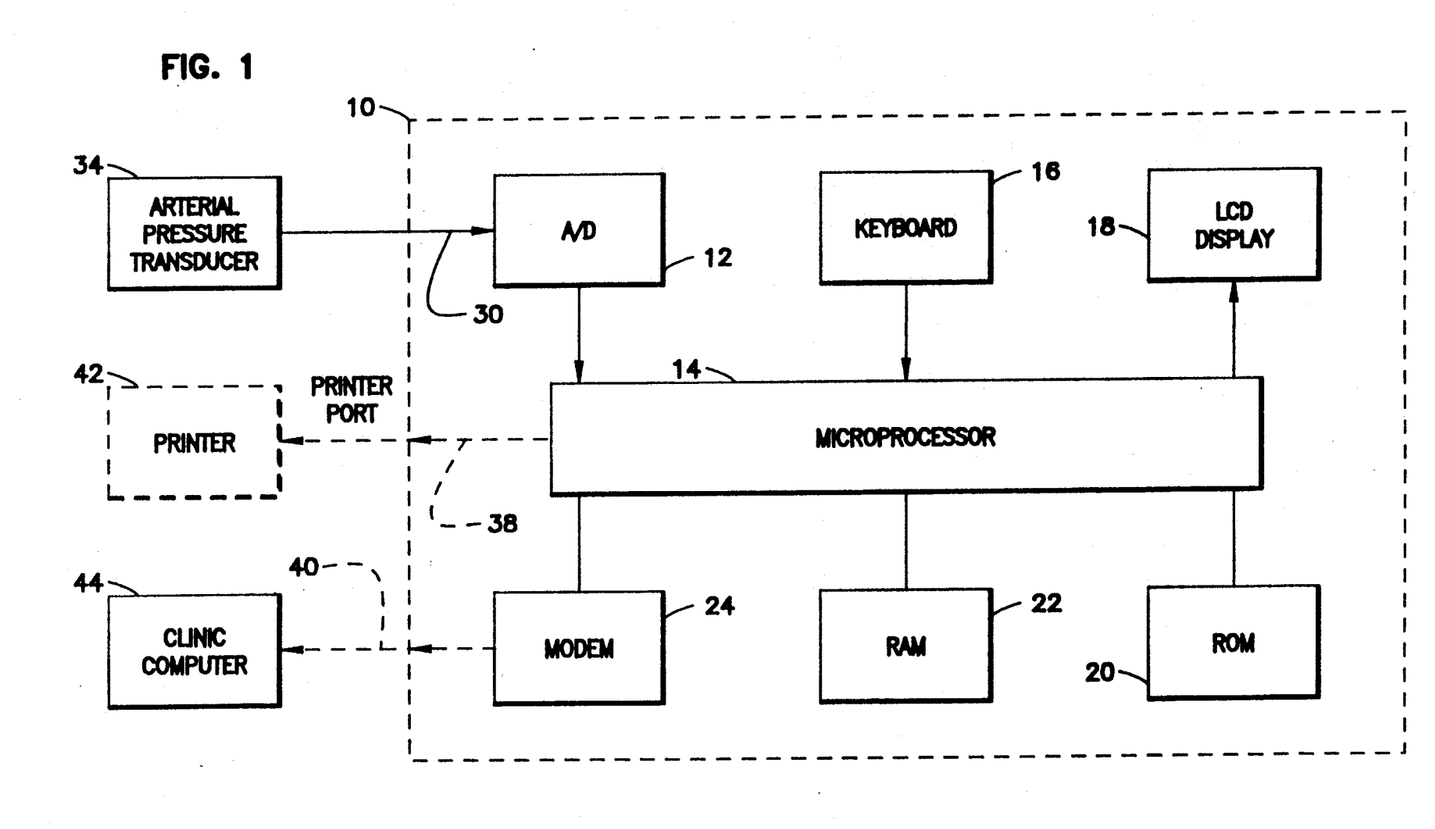
FIG. 1 is a schematic block diagram of the cardiac output meter according to the present invention.

The cardiac output meter 10 according to the present invention is shown in schematic block diagram form in FIG. 1. The meter 10 includes an analog to digital convertor (A/D) 12, preferably 12-bit, a microprocessor unit 14, for instance a 30386 model by Intel, a keyboard input 16, display 18, ROM 20, RAM 22 and modem 24. An input port 30 is provided to receive analog signal input from an arterial pressure transducer 34. A printer output port 38 and a telephone port 40 are provided from microprocessor 14 and modem 24, respectively.

Where the arterial waveform is obtained invasively, transducer 34 is preferably a Statham P23Db pressure transducer, connected to a brachial artery by an 18-gauge, 2-inch Teflon catheter. This catheter-transducer system has an undamped natural frequency higher than 25 HZ and a damping coefficient less than 0.5, providing an acceptable frequency response. It shall be understood, however, that while the brachial artery is preferred, other arterial peripheral locations for obtaining the pulse pressure contour can be substituted.

A non-invasive transducer 34 unit can also be used, for example, a finger-cuff transducer unit using a counter pulsation technique wherein the waveform is detected by balancing the pressure in the finger cuff with that in the finger. A commercially available finger-cuff transducer unit is the Finapres ® Continuous NIBP Monitor Model 2300, from Ohmeda Monitoring Systems division of the BOC Group, Inc., 355 Inverness Drive South, Engelwood, Colo. 80112-5810. The Finapres ® device produces an analog output signal which is equivalent to the output signal of the P23Db pressure transducer, and can be fed through port 30 to A/D converter 12. Another non-invasive transducer unit acceptable for use with the present invention is the Model 506 Non-invasive Patient Monitor from Criticare Systems, Inc., 20900 Swenson Drive, Suite 398, Waukesha, Wisc. 53186.

Figures 2A, 2B:
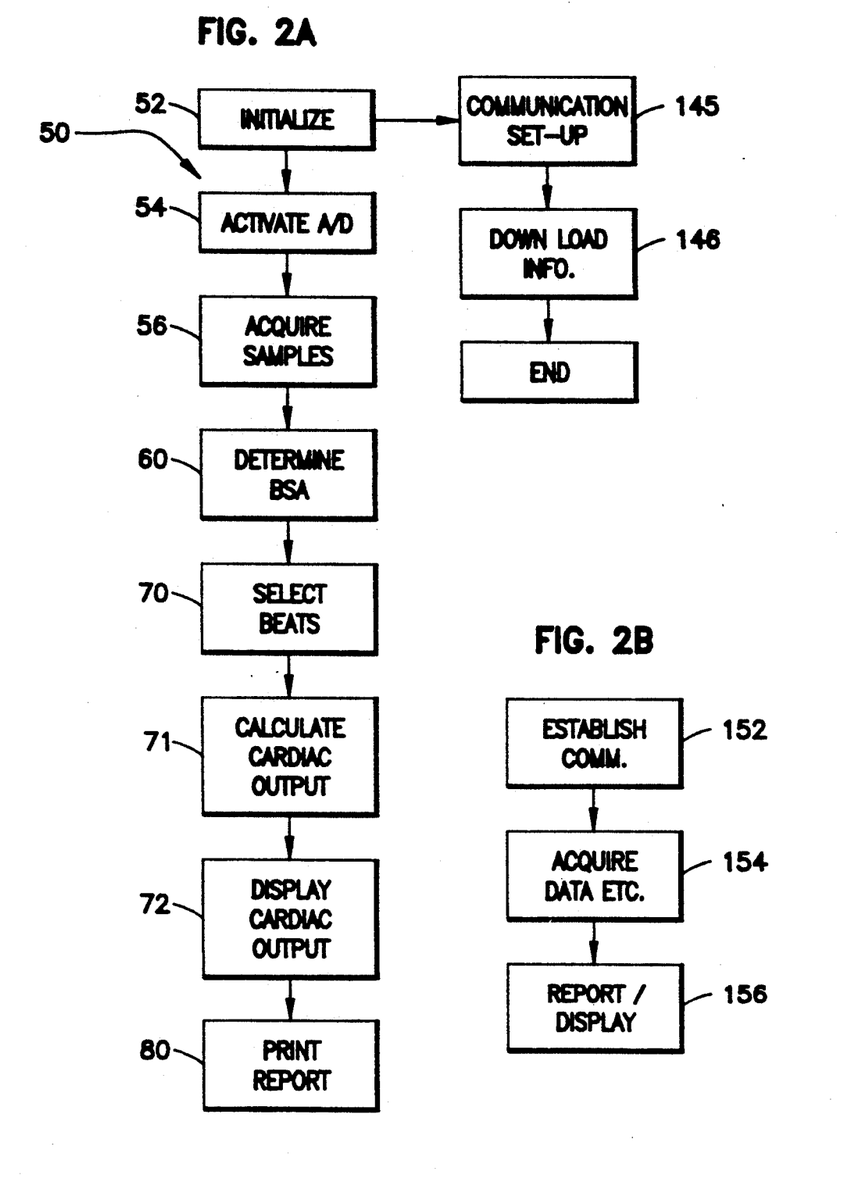
FIG. 2A and 2B comprise a schematic flow chart of the software of the present invention.

The software component 50 of the meter 10 is illustrated in block diagram flow-chart form in FIGS. 2A and B. Software within meter 10 is preferably maintained in ROM 20 and is referenced by microprocessor 14. Alternatively, software 50 can be stored in magnetic or other digital form on a floppy computer disk or equivalent connected so as to be accessed by the microprocessor.

Figure 3:
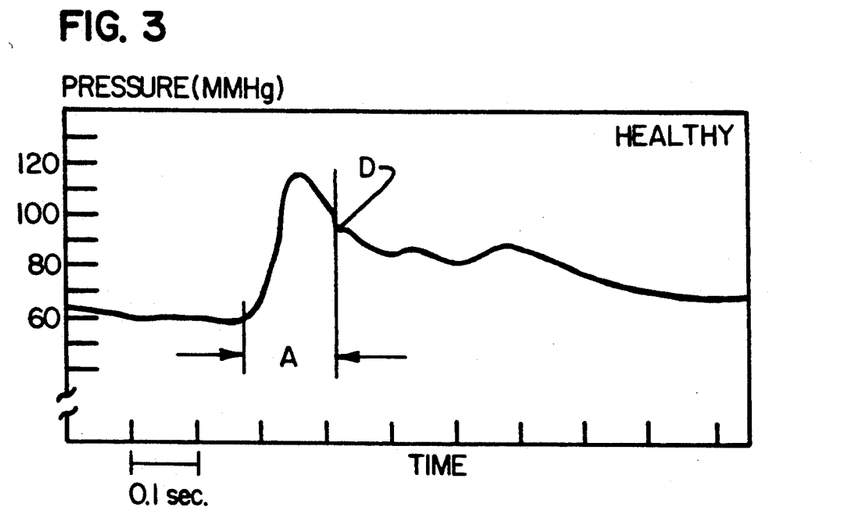
FIG. 3 is illustrative example of typical arterial pulse contours in healthy patients.
Figure 4:
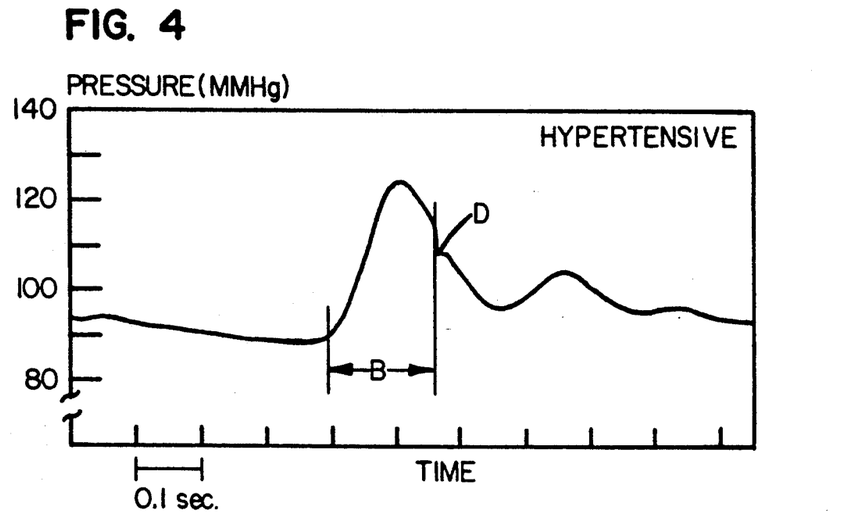
FIG. 4 is illustrative example of typical arterial pulse contours in diseased patients.

Software 50 runs on microprocessor 14 to control the acquisition of arterial pressure pulse data, and to perform other meter functions, as described below. An initialization and mode select routine 52 is provided for initializing microprocessor 14, including prompting the user to enter patient information, including the patient's age, height (in centimeters) and weight (in kilograms), and/or body surface area (in square meters). Routine 52 further allows either the meter mode or communication mode to be selected. If the meter mode is selected, A/D convertor 12 is activated (54) to digitize an analog pressure pulse signal generated by transducer 34. FIGS. 3 and 4 illustrate typical brachial artery pulse pressure contours for normotensive and hypertensive patients, respectively.

The present invention uses an A/D sampling rate of 200 samples/second, which is satisfactory to capture the highest frequency components of interest in the pressure pulse. It shall be understood, however, that higher or lower sampling rates may be used, and that the invention is in no way limited to the 200 samples/second rate. Routine 56 provides that the artery is metered for approximately 30 seconds, producing in the range of 25 to 60 digitized pulses, depending on the heart rate. The stream of digitized pulses are stored in RAM 22 in the form of a continuous series of periodic time dependent data byte samples, with each data byte corresponding to the instantaneous pressure of the artery.

Routine 60 determines body surface area by standard formula, or alternatively looks it up in a nomogram table stored in memory, using the patient's height and weight data. Alternatively, body surface area can be determined by the physician or other care giver and entered into the meter at routine 52, as noted above. A formula for determining BSA known to work in connection with the present invention is:

$$BSA\ (m^{-2}) = 0.0072 \times weight\ 0.425^{0.425} \times height^{0.725}\ \text{where weight is in kilograms and height is in centimeters.}$$

A monogram table known to work with the present invention is found in the Merck Manual, 12th edition, 1972 on page 1840 (reproduced from Wm. Brothby and R. B. Sandford, Boston Medical and Surgical Journal, Vol. 185, p. 337, 1921).

Selection routine 70 analyzes the recorded wave data to determine ejection time. First, routine 70 selects a group of consecutive representative beats (it has been found that six to ten beats are preferred but the number used is in no way critical to the invention) preferably of comparatively low noise content. Representative beats are identified by establishing windows of permissible heart rate and mean arterial pressure values whereby abnormally fast or slow heartbeats, or high or low pressures can be rejected. The routine can thus pick the series of beats which is most representative. The heart rate (HR) is also determined by this routine, by counting the number of beats per unit time. Where possible it is preferable that the windows be tailored to the patient, thus allowing more precise selection of representative beats.

Routine 70 determines ejection time as follows. First, the heart waveforms are marked for analysis. When marked manually, a clinician can identify the onset of systole and the upstroke, by correlating to the first heart sound $S_1$. The end of systole, signalled by diastole, can be found manually by correlating to the second heart sound $S_2$. Ejection time is then determined by the time between the occurrence of systole to diastole. For example, in FIGS. 3 and 4 ejection time is marked by the respective segments A and B, assuming a waveform obtained proximate the heart.

The present invention uses a software analysis algorithm at routine 70 to predict and select the segment in each wave most probably corresponding to ejection time. Routine 70 searches the waveform data for the waveform upstroke marking systole, and then for the dicrotic notch (D), looked for after the peak of the systolic upstroke, and marks the onset of diastole just before the location of the dicrotic notch on the wave. The ejection time (ET) is then determined from the location of the onset of systole and diastole. Transit time effects due to the distance between the aorta and the measurement site are taken into account in the ejection time measurement by moving back a predetermined interval (depending on where with arterial waveform is measured in the arterial system) from the trough of the dicrotic notch to determine end of systole for the purposes of this ejection time determination. The ejection time is thus the time between the upstroke (beginning of systole) and this point marking the end of systole. For waveforms obtained from the femoral artery, an interval of 25 milliseconds has been found satisfactory to compensate for transit time effects. Shorter or longer intervals would be appropriate for waveforms obtained closer to or further from the heart, respectively.

Alternatively, device 10 can include means for digitizing an analog signal representing the heart sounds, software for identifying the first and second heart sounds $S_1$ and $S_2$, and for correlating them to the digitized arterial waveform to identify the onset of systole and diastole.

Routine 71 calculates stroke volume using the following formula:

$$SVA = -6.6 + (0.25 \times ET) + (40.4 \times BSA) - (0.51 \times Age) - (0.62 \times HR),$$

where SVA equals stroke volume in ml/beat, ET is ejection time in msec, BSA is body surface area in square meters and HR is heart rate (bpm); using the heart rate (HR), body surface area (BSA), ejection time (ET) and age for the subject. Cardiac output can be determined by multiplying heart rate (HR) times stroke volume (SVA).

Routine 72 is provided to indicate via display 18 the calculated value, either graphically, for instance a bar graph showing the magnitude of cardiac output or stroke volume on a scale, or by displaying a corresponding numerical value, on the LCD display. Routine 80 is provided to report the analysis results on an optional printer 42.

Meter 10 also includes communications capability, whereby the measured cardiac output data (or, if desired other stored vascular parameters) may be communicated to further computer equipment 44 in a clinic or hospital, such as a personal computer or minicomputer. Accordingly, meter 10 may be used by a patient at home with measured cardiac output being transmitted back to a treating hospital or clinic for review or for further analysis. For this purpose software 50 provides a communications mode including routines 145 and 146, which provide for establishing a communication link with remote system and for downloading the cardiac output measurement.

As shown in FIG. 1, a clinic or hospital computer 44 is provided to communicate with meter 10 using a standard modem-telephone link. FIG. 2B illustrates in diagrammatic form the software 150 provided for clinic computer 44. A routine 152 is provided for establishing the communication link with meter 10. Computer 44 preferably includes an auto-answer modem so that meter 10 may establish communication therewith with a minimum of effort. Data acquisition routine 154 is provided to receive one or more cardiac output values, which may be stored in RAM 22. Report/display routine 156 provides reporting or display of downloaded cardiac output values for use by the hospital or clinic staff.

Figure 5:
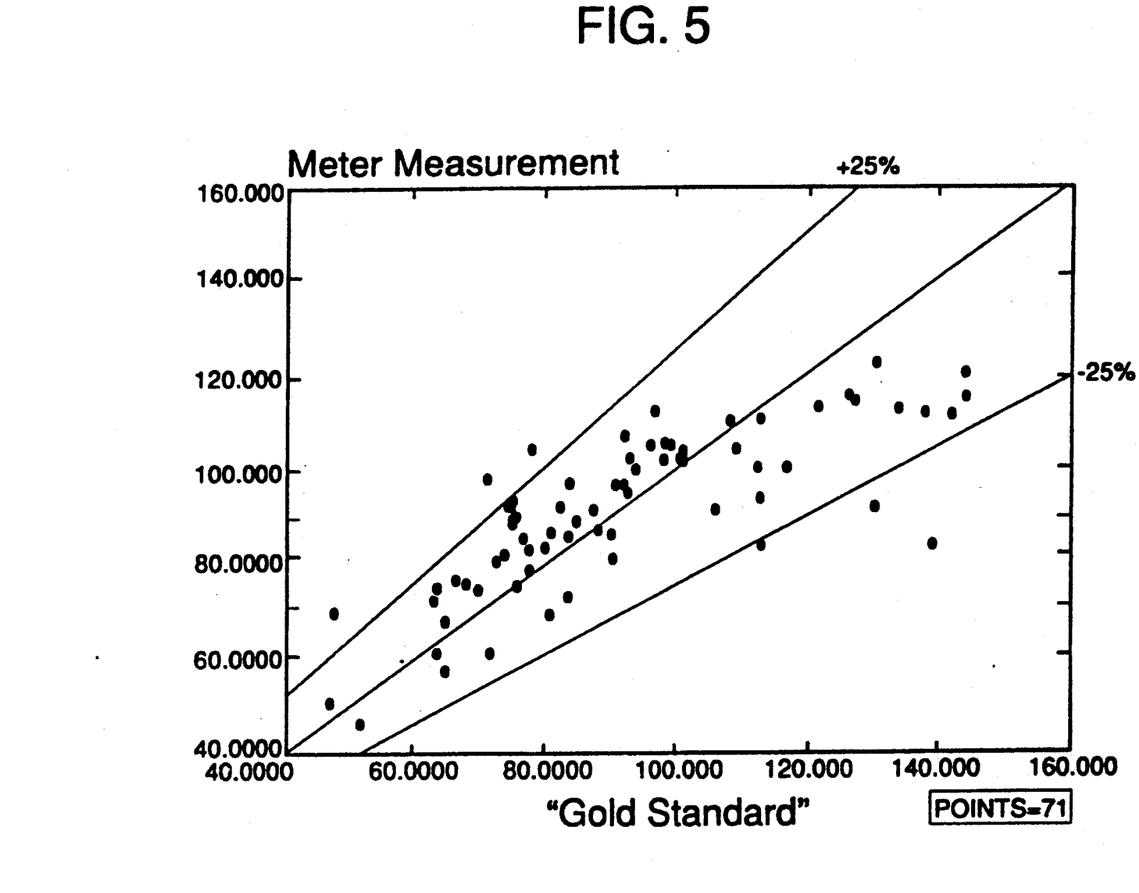
FIG. 5 is a scatterplot of invasively measured stroke volume using thermal dilution vs. stroke volume obtained from the present invention for 71 cases which formed the basis for the development of the present invention.

FIG. 5 is a scatterplot of invasively measured stroke volume (in ml/heart beat) using thermodilution (the "Gold Standard") vs. stroke volume (in ml/heart beat) measured using the meter of the present invention, for 71 cases. These 71 cases formed the basis for development of the present invention, which included a multiple linear regression fit. FIG. 5 shows that in 90% of the cases, there was less than a (+ −)25% difference between the cardiac output measurement obtained by thermodilution and that obtained using the present invention.

Figure 6:
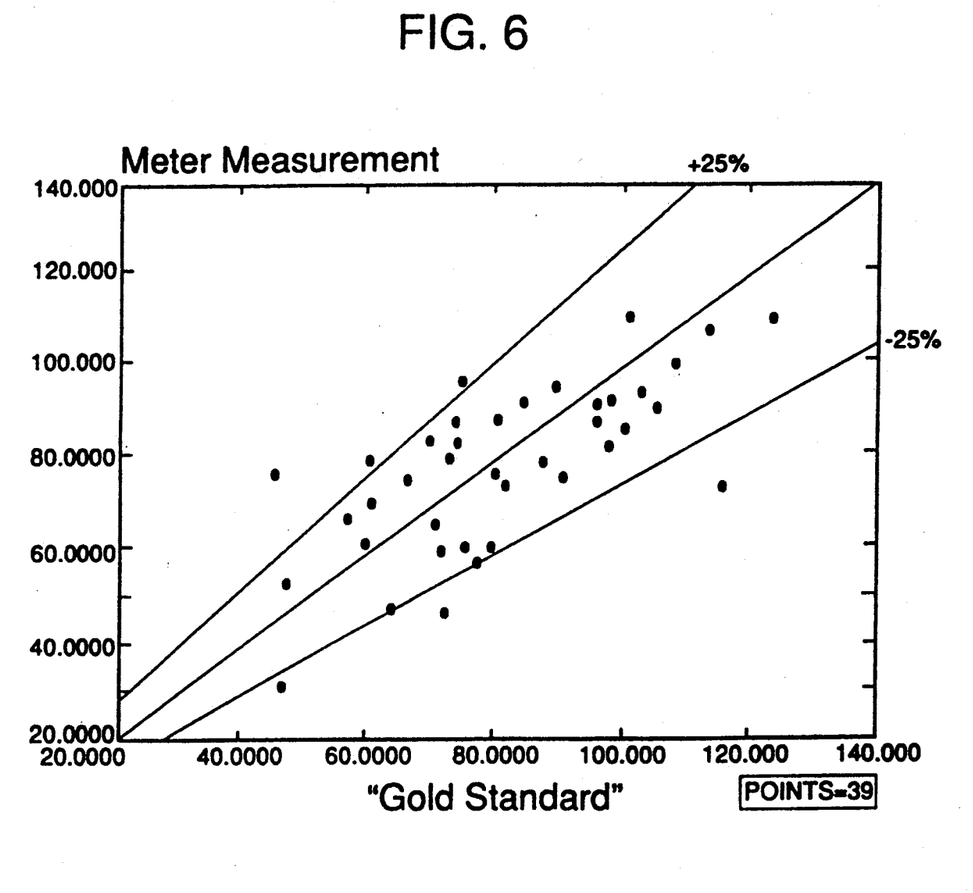
FIG. 6 is a scatterplot of invasively measured stroke volume using thermodilution vs. stroke volume measured using the present invention for 39 separate, independent cases used to test the accuracy of the meter of the present invention.

FIG. 6 is a scatterplot of invasively measured stroke volume (in ml/heart beat) using thermodilution (the "Gold Standard") vs. stroke volume (in ml/heart beat) measured using the meter of the present invention, for 39 separate, independent cases. The subjects of this study ranged from 19-75 in age. FIG. 6 shows that in 88% of the cases, there was less than a (+ −)25% difference between the cardiac output measurement obtained by thermodilution and that obtained using the present invention. The accuracy of the meter, as currently understood from the cases against which it has been tested, is thus adequate to provide a cardiac output measure adequate for many applications wherein an approximate measure is acceptable. This accuracy compares favorably against the 10-20% reproducibility of the most accurate dilution techniques.

The present invention also includes a method for measuring stroke volume/cardiac output. The method includes the following steps:

1) Measuring, either noninvasively or invasively, an arterial blood pressure waveform, from which the ejection time of the heart is determined, taking into account transit time effects between the aorta and the measurement site;
2) Measuring the heart rate;
3) Determining the body surface area by standard formula or by nomogram, using the subject's height and weight;
4) Determining stroke volume substantially in accordance with the following formula:

$$SVA = -6.6 + 0.25 \times ET + 40.4 \times BSA - 0.51 \times Age - 0.62 \times HR,$$

where SVA equals stroke volume in ml/beat, ET is ejection time in msec, BSA is body surface area in square meters and HR is heart rate (bpm); and
5) Calculating cardiac output by multiplying heart rate HR times stroke volume (SVA).

It is currently contemplated that the formula for determining cardiac output set forth herein will be further refined and adjusted as further data is collected and/or as adjustments to constants and factors are determined to produce more accurate determinations of cardiac output. The formula may be adjusted by performing a multiple linear regression to fit a new formula on "Gold Standard" data. Accordingly, it shall be understood that the basic structure of the formula is to be emphasized. Also, it shall be understood that both cardiac output per se (SVA×heart rate) and SVA are considered measures of cardiac output for the purpose of the claims appended hereto. Moreover, it is contemplated that many changes and modifications may be made to the method and apparatus of the invention without departing from the spirit and scope of the claims appended hereto.

We claim:

1. A cardiac output measurement system for processing a blood pressure waveform obtained from a patient to determine the patient's cardiac output from the waveform and the patient's age and body surface area, the blood pressure waveform containing heartbeat signals, comprising:

a) transducer means for measuring an arterial blood pressure waveform obtained from a patient and generating a corresponding analog signal;

b) means for digitizing the analog signal generated by the transducer means resulting in a digitized blood pressure waveform;

c) waveform marking means for searching a heart beat signal in the digitized blood pressure waveform, for marking a segment of the heart beat signal corresponding to systole, and for determining an ejection time signal by measuring the duration of said segment;

d) heart rate measuring means for counting the number of heart beat signals per unit time in said digitized blood pressure waveform to produce a heart rate signal for the patient;

e) means for determining a measure of cardiac output using at least the ejection time, the heart rate signal, and body surface area and age of the patient; and f) means for indicating the measure of cardiac output.

2. The system of claim 1 wherein the waveform marking means includes means for selecting a group of representative heart beat signals, according to predetermined criteria, from said digitized blood pressure waveform signal.

3. The system of claim 2 wherein the predetermined criteria include criteria for excluding abnormally fast heartbeat signals, and abnormally slow heartbeat signals, from the selected group.

4. The system of claim 1 further wherein the means for determining a measure of cardiac output includes means for determining stroke volume substantially in accordance with the following formula:

$$SVA = -6.6 + 0.25 \times ET + 40.4 \times BSA - 0.51 \times Age - 0.62 \times HR,$$

where SVA signals stroke volume in ml/beat, ET is ejection time in msec, BSA is body surface area in square meters and HR is heart rate (bpm).

5. The system of claim 1 further wherein said means for indicating comprises means for displaying a bar graph of the magnitude of cardiac output.

6. A cardiac output measurement system for processing a blood pressure waveform obtained from a patient to determine the patient's cardiac output from the waveform and the patient's age and body surface area, the blood pressure waveform containing heart beat signals, comprising:

a) transducer means for measuring an arterial blood pressure waveform obtained form the human patient and generating a corresponding analog signal;

b) means for digitizing the analog signal generated by the transducer means resulting in a digitized blood pressure waveform;

c) heart beat signal selection means for processing said digitized blood pressure waveform to select a group of representative heart beat signals from the digitized blood pressure waveform signal, said group selected according to predetermined criteria whereby unwanted heart beat signals are filtered out of the digitized blood pressure waveform;

d) waveform marking means for searching a heart beat signal in the selected group, for marking a segment of the heart beat signal corresponding to systole, and for determining an ejection time signal by measuring the duration of said segment;

e) heart rate measuring means for counting the number of heart beats per unit time in the selected group to produce a heart rate signal for the patient;

f) means for determining a measure of cardiac output using at least the ejection time, the heart rate signal, and body surface area and age of the patient; and g) means for indicating the measure of cardiac output.

7. The system of claim 6 further wherein the means for determining a measure of cardiac output includes means for determining stroke volume substantially in accordance with the following formula:

$$SVA = -6.6 + 0.25 \times ET + 40.4 \times BSA - 0.51 \times \times Age - 0.62 \times HR,$$

where SVA signals stroke volume in ml/beat, ET is ejection time in msec, BSA is body surface area in square meters and HR is heart rate (bpm).

8. A noninvasive cardiac output measurement system for processing a blood pressure waveform obtained from a patient to determine the patient's cardiac output from the waveform and the patient's age and body surface area, the blood pressure waveform containing heart beat signals, comprising:

non-invasive transducer means for measuring an arterial blood pressure waveform obtained from the human patient and generating a corresponding analog signal;

a digital storage device;

a digitizer means for digitizing the analog signal for a series of the patient's heart beats to produce a digital blood pressure waveform and for storing the digitized blood pressure waveform signal in said digital storage device;

first digital processing means connected to said digital storage device for processing the digitized blood pressure waveform signal to:

(a) select a group of representative heart beat signals from the digitized blood pressure waveform signal, (b) count the number of heart beats per unit time in the selected group to produce a heart rate signal for the patient, (c) search a heart beat signal in the selected group for a first event marking the beginning of systole and a second event marking the end of systole, and determine an ejection time signal by measuring the time between the first and second events taking into account transit time effects;

second digital processing means for receiving a weight and a height for the patient and generating a body surface area value indicative of the patient's body surface area;

means for determining a measure of cardiac output from the heart rate signal, the ejection time signal, an age and the body surface area value and for generating an output signal indicative of the patient's cardiac output; and display means responsive to the output signal for displaying a magnitude of the output signal.

9. The system of claim 8 further wherein the means for determining a measure of cardiac output includes means for determining stroke volume substantially in accordance with the following formula:

$$SVA = -6.6 + 0.25 \times ET + 40.0 \times BSA - 0.51 \times Age - 0.62 \times HR,$$

where SVA equals stroke volume in ml/beat, ET is ejection time in msec, BSA is body surface area in square meters and HR is heart rate (bpm).

10. The system of claim 8 further wherein said noninvasive transducer means comprises:
   a finger-cuff transducer means for converting a blood pressure waveform obtained from a patient's finger to a corresponding analog signal blood pressure waveform signal, the finger-cuff transducer means using a counter pulsation technique wherein the waveform is detected by balancing the pressure in the finger cuff with that in the patient's finger.

11. They system according to claim 8 further wherein the first event is the upstroke of the heart beat signal indicating the onset of systole, and the second event is the dicrotic notch on the heart beat signal, indicating the onset of diastole.

12. A method of determining cardiac output in a patient, comprising steps of:
   a) measuring over time an arterial blood pressure of the patient to provide an arterial blood pressure waveform, the blood pressure waveform containing heart beat signals;
   b) digitizing the blood pressure waveform and storing it in a storage device;
   c) searching a heart beat signal in the digitized blood pressure waveform, marking a segment of the heart beat signal corresponding to systole, and determining an ejection time signal by measuring the duration of the segment;
   d) measuring the heart rate by counting the number of heart beats per unit time using the heart beat signals to produce a heart rate signal for the patient;
   e) determining a body surface area of the patient; and
   f) determining a measure of cardiac output of the patient substantially in accordance with the ejection time, age, body surface area and heart rate of the patient.

13. The method of claim 12 wherein the step of determining a measure of cardiac output is determined substantially in accordance with the following formula:

$$SVA = -6.6 + 0.25 \times ET + 40.4 \times BSA - 0.51 \times Age - 0.62 \times HR,$$

where SVA equals stroke volume in ml/beat, ET is ejection time in msec, BSA is body surface area in square meters and HR is heart rate (bpm).

14. A method of determining cardiac output in a human patient, comprising the steps of:
   a) measuring over time an arterial blood pressure waveform of the patient to provide an arterial blood pressure waveform, the waveform containing heart beat signals;
   b) digitizing the blood pressure waveform and storing it in a storage device;
   c) selecting a group of consecutive representative heart beat signals from the digitized blood pressure waveform signal, said group selected according to predetermined criteria so that unwanted heart beat signals are filtered from the waveform;
   d) searching a heart beat signal in the selected group, marking a segment of the heart beat signal corresponding to systole, and determining an ejection time signal by measuring the duration of the segment;
   e) measuring the heart rate by counting the number of heart beats per unit time of the selected group to produce a heart rate signal for the patient;
   f) determining a body surface area of the patient; and
   g) determining a measure of cardiac output of the patient substantially in accordance with the ejection time, age, the body surface area and the heart rate of the patient.

15. The method of claim 14 wherein the step of determining a measure of cardiac output is determined substantially in accordance with the following formula:

$$SVA \times -6.6 + 0.35 \times ET + 40.4 \times BSA - 0.51 \times Age - 0.62 \times HR,$$

where SVA equals stroke volume in ml/beat, ET is ejection time in msec, BSA is body surface area in square meters and HR is heart rate (bpm).

* * * * *

UNITED STATES PATENT AND TRADEMARK OFFICE
CERTIFICATE OF CORRECTION

PATENT NO. : 5,241,966

DATED : September 7, 1993

INVENTOR(S) : Finkelstein et al.

It is certified that error appears in the above-indentified patent and that said Letters Patent is hereby corrected as shown below:

Column 1, line 20, delete "cardiovasculature" and insert --cardiovascular system-- therefor.

Column 1, line 34, delete "patients size and" and insert --patient's size are-- therefor.

Column 1, line 37, delete "and which".

Column 2, beginning on line 31, replace the formula with:
$SVA = -6.6 + (0.25 \times ET) + (40.4 \times BSA) - (0.51 \times Age) - (0.62 \times HR)$ Column 2, line 36, after "subject" insert --in years--.

Column 2, line 60, delete "thermal" and insert --dye-- therefor.

Column 3, line 31-32, delete "division of the BOC Group, Inc., 355 Inverness Drive South, Englewood, Colo. 80112-5810." and insert --A BOC Health Care Company, Ohmeda Drive, Madison, Wisc. 53707.-- therefor.

Column 3, line 55, after "age" insert --(in years).-- therefor.

Column 4, line 18, replace the formula with:
$BSA\ (m-2) = 0.0072 \times weight^{0.425} \times height^{0.725}$ where weight is in kilograms and height is in centimeters.

Column 5, line 23, after "square meters" insert --, Age is the age of the subject in years,--.

Column 5, delete lines 24-27 in their entirety.

UNITED STATES PATENT AND TRADEMARK OFFICE
CERTIFICATE OF CORRECTION

PATENT NO. : 5,241,966

DATED : September 7, 1993

INVENTOR(S) : Finkelstein et al.

It is certified that error appears in the above-indentified patent and that said Letters Patent is hereby corrected as shown below:

Column 6, line 10, delete "in" and insert --of age-- therefor.

Column 6, line 21, after "accurate" insert --invasive-- therefor.

Column 6, line 37, replace the formula with:
$$SVA = -6.6 + (0.25 \times ET) + (40.4 \times BSA) - (0.51 \times Age) - (0.62 \times HR)$$

Column 6, line 41, after "meters" insert --, Age is the age of the subject in years,--.

Col. 7,
Claim 4, line 6, replace the formula with:
$$SVA = -6.6 + (0.25 \times ET) + (40.4 \times BSA) - (0.51 \times Age) - (0.62 \times HR).$$

Claim 4, line 11, after "meters" insert --, Age is the age of the subject in years,--.

Col. 8,
Claim 7, line 6, replace the formula with:
$$SVA = -6.6 + (0.25 \times ET) + (40.4 \times BSA) - (0.51 \times Age) - (0.62 \times HR)$$

Col. 8,
Claim 7, line 11, after "meters" insert --, Age is the age of the subject in years,--.

Col. 8,
Claim 9, line 6, replace the formula with:
$$SVA = -6.6 + (0.25 \times ET) + (40.4 \times BSA) - (0.51 \times Age) - (0.62 \times HR)$$

Col. 9,
Claim 9, Line 11, after "meters" insert --, Age is the age of the subject in years,--.

Claim 11, line 1, delete "they" and insert --the-- therefor.

Col. 10,
Claim 13, Line 4, replace the formula with:
$$SVA = -6.6 + (0.25 \times ET) + (40.4 \times BSA) - (0.51 \times Age) - (0.62 \times HR)$$

UNITED STATES PATENT AND TRADEMARK OFFICE
CERTIFICATE OF CORRECTION

PATENT NO. : 5,241,966

DATED : September 7, 1993

INVENTOR(S) : Finkelstein et al.

It is certified that error appears in the above-indentified patent and that said Letters Patent is hereby corrected as shown below:

Col. 10,
Claim 13, line 9, after "meters" insert --, Age is the age of the subject in years,-- therefor.

Claim 15, line 5, replace the formula with:
SVA = -6.6 + (0.25 × ET) + (40.4 × BSA) - (0.51 × Age) - (0.62 × HR)
Col. 10,
Claim 15, line 10, after "meters" insert --, Age is the age of the subject in years,--.

Signed and Sealed this

Seventeenth Day of September, 1996

Attest:

BRUCE LEHMAN

Attesting Officer    Commissioner of Patents and Trademarks